United States Patent
Jubin, Jr. et al.

(10) Patent No.: US 6,867,312 B1
(45) Date of Patent: Mar. 15, 2005

(54) PROPYLENE OXIDE PROCESS

(75) Inventors: John C. Jubin, Jr., West Chester, PA (US); Roger A. Grey, West Chester, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/802,690

(22) Filed: Mar. 17, 2004

(51) Int. Cl.$^7$ ............................................. C07D 301/03
(52) U.S. Cl. ...................................... 549/523; 549/532
(58) Field of Search ................................. 549/532, 523

(56) References Cited

U.S. PATENT DOCUMENTS

| | | | |
|---|---|---|---|
| 5,646,314 A | 7/1997 | Crocco et al. | |
| 5,859,265 A | 1/1999 | Muller et al. | |
| 6,005,123 A | 12/1999 | Dessau et al. | |
| 6,008,388 A | 12/1999 | Dessau et al. | |
| 6,008,389 A | 12/1999 | Grosch et al. | |
| 6,106,797 A | 8/2000 | Muller et al. | |
| 6,555,493 B2 | 4/2003 | Cooker et al. | |
| 6,576,214 B2 | 6/2003 | Zhou et al. | |

FOREIGN PATENT DOCUMENTS

| | | |
|---|---|---|
| DE | 19600709 | 1/1996 |
| DE | WO9725143 | 7/1997 |
| JP | 4-352771 | 5/1991 |
| JP | H8-269029 | 3/1995 |
| JP | H8-269030 | 3/1995 |

*Primary Examiner*—Amelia A. Owens
(74) *Attorney, Agent, or Firm*—William C. Long

(57) ABSTRACT

Propylene oxide is formed in a two step reaction wherein in a first step oxygen and hydrogen are reacted in the absence of propylene to form hydrogen peroxide and in a second step propylene is reacted with the formed hydrogen peroxide to form propylene oxide, the same solid noble metal on TS-1 catalyst being used to catalyze the reaction in each step.

9 Claims, 1 Drawing Sheet

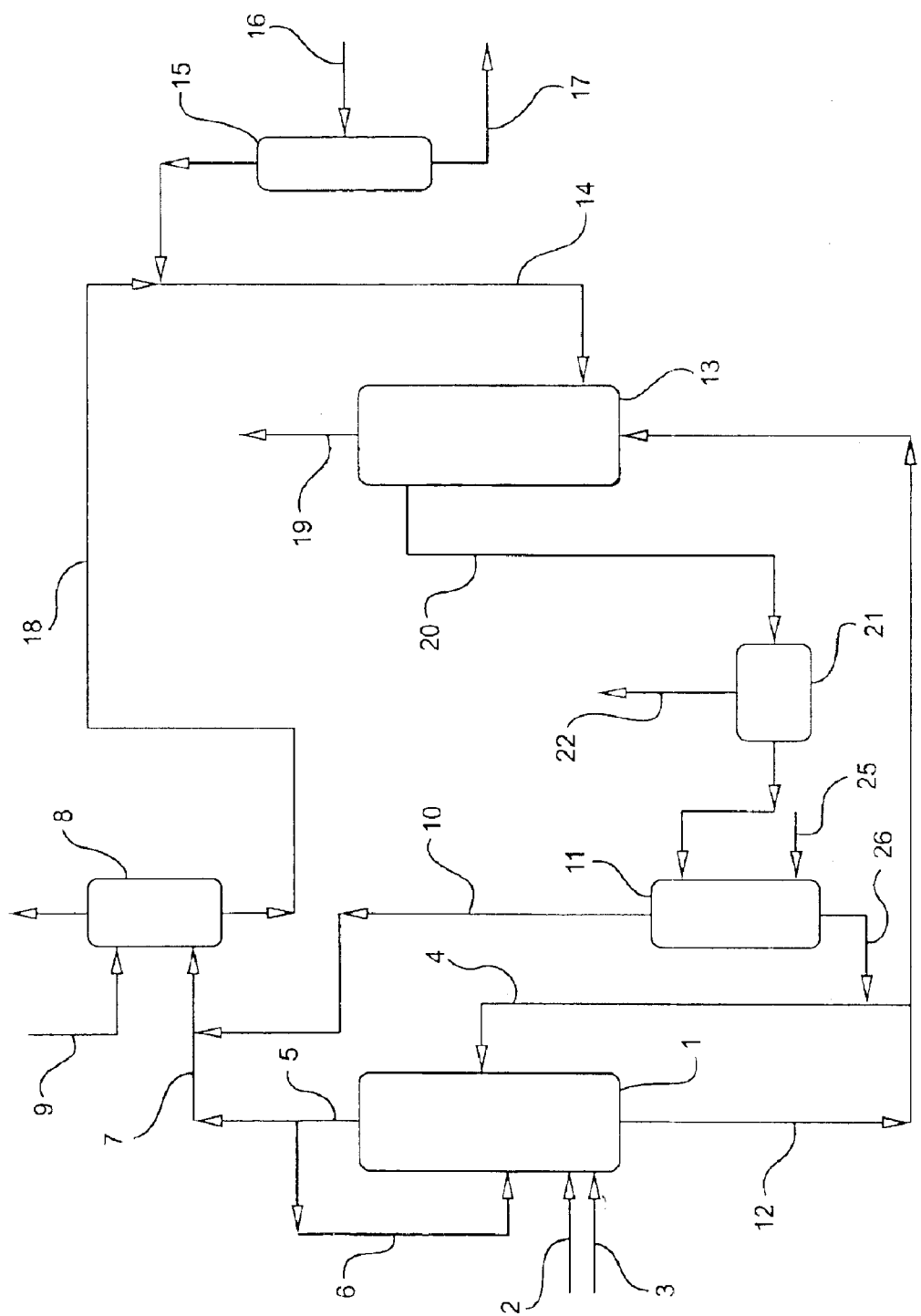

PROPYLENE OXIDE PROCESS

BACKGROUND OF THE INVENTION

1. Field of the Invention

The present invention relates to a process for the production of propylene oxide wherein in a first reaction oxygen and hydrogen are reacted to form hydrogen peroxide and in a second reaction the formed hydrogen peroxide from the first reaction is reacted with propylene to form propylene oxide, each reaction being carried out in slurry of the same catalyst with propylene being essentially excluded from the first reaction.

2. Description of the Prior Art

It is known in the prior art to form propylene oxide by reaction of propylene, hydrogen and oxygen in a slurry comprised of a noble metal promoted TS-1 catalyst. See, for example, Kokai No. 4-352771, U.S. Pat. No. 6,555,493, and the like.

A disadvantage has been that during the reaction propylene reacts to a significant extent with the hydrogen reactant to form propane, this reaction representing a significant process yield loss.

It is further known to react hydrogen and oxygen using a palladium catalyst to form hydrogen peroxide and, after separation of the catalyst, to react the formed hydrogen peroxide with a chemical feed, which may include propylene, to form another product such as propylene oxide, phenol, an oxime or the like. See U.S. Pat. No. 6,576,214.

Insofar as the prior art is concerned, it is believed that the art does not describe or suggest the improved process of the present invention or the beneficial results achieved thereby.

SUMMARY OF THE INVENTION

In accordance with the present invention, propylene oxide is formed in a plurality of separate steps with the same catalyst being employed in each step. In a first step, oxygen and hydrogen are reacted to form hydrogen peroxide, the reaction being carried out in the essential absence of propylene. In a separate second step the formed hydrogen peroxide from the first step is reacted with propylene using the catalyst from the first reaction to form propylene oxide. By carrying out the first reaction step in the absence of propylene, the formation of propane is avoided. By using the same catalyst in both reactions, important efficiencies of operation are achieved. While it is preferred to carry out the invention as a continuous process using a plurality of separate reactors, it is possible to carry the process out in a single reactor in batch fashion.

DESCRIPTION OF THE DRAWING

The accompanying drawing is a schematic representation of a practice of the invention.

DETAILED DESCRIPTION

The invention can, perhaps, best be described by reference to the accompanying drawing.

Referring to the attached figure, reactor 1 represents a conventional reactor suitable for the reaction of hydrogen and oxygen to form hydrogen peroxide. In reactor 1, the reaction is carried out in a slurry of suitable solid catalyst, such as palladium promoted TS-1, in a solvent such as methanol or methanol/water.

Introduced to reactor 1 via line 2 is feed hydrogen and via line 3 is feed oxygen. A combined stream of solvent and catalyst is introduced to reactor 1 via line 4. In reactor 1, conditions are maintained whereby hydrogen and oxygen react to form hydrogen peroxide. It is an important feature of the invention that propylene essentially be excluded from reactor 1 during hydrogen peroxide formation in order to avoid propane formation.

A vapor mixture is separated overhead from reactor 1 via line 5 with a portion recycled via line 6 and the remainder passing via line 7 to absorber 8. Solvent such as methanol which provides the liquid medium in each of the reactors is introduced via line 9 to absorber 8. Also introduced to absorber 8 via lines 10 and 7 is the overhead from stripper 11 which is described hereinafter.

Liquid reaction mixture comprised of product hydrogen peroxide in the solvent/catalyst slurry is removed via line 12 and passed to reactor 13, a portion being recycled via line 4 after appropriate cooling (not shown) to remove heat of reaction.

The catalyst which is employed in both reactor 1 and reactor 13 can be a solid noble metal promoted catalyst such as palladium on TS-1 as described in Kokai No. 4-352771, U.S. Pat. No. 6,55,493 and the like. Generally speaking, the concentration of product hydrogen peroxide in the reactor 1 reaction mixture is maintained at a low level, e.g. 0.1 to 5 wt % with a high circulation rate of the reaction mixture from reactor 1 to reactor 13 to assure reasonable rates of reaction and high reaction selectivity.

Propylene reactant is introduced into reactor 13 via line 14. A $C_3$ splitter 15 is provided which separates a mixed $C_3$ fraction introduced via line 16 into a propane stream removed via line 17 and the propylene feed to reactor 13.

Also fed to reactor 13 via lines 14 and 18 is a solvent stream containing absorbed components from absorber 8.

In reactor 13, propylene oxide is formed by reaction of propylene and the hydrogen peroxide from reactor 1, the reaction taking place in the catalyst/solvent reaction mixture slurry from reactor 1. An overhead stream which comprises various components such as oxygen, hydrogen, propylene and propylene oxide product is separated via line 19 and passed to a separation and recovery facility (not shown) wherein the various components are recovered and, where applicable, recycled.

The slurry reaction mixture is removed from reactor 13 via line 20 and passed to filter 21 wherein a partial filtration takes place, that is solids are separated from a portion of the reaction mixture and this portion from which solids have been separated is removed via line 22. The solids—free stream is passed to conventional treatment (not shown) wherein product propylene oxide is recovered and the various other components are recovered and, where appropriate, recycled.

The remainder of the reaction mixture comprising a slurry of the catalyst particles is passed to stripper 11 wherein the mixture is stripped with an inert stripping gas which is introduced via line 25. The stripping gas effectively strips unreacted propylene from the reaction mixture, the stripper overhead passing via line 10 to absorber 8 and the stripper bottoms is passed via lines 26 and 4 back to reactor 1 for further production of hydrogen peroxide.

As a result of the described process, the undesirable reaction of hydrogen with propylene to form propane is substantially avoided since propylene is essentially excluded from reaction zone 1 and hydrogen is substantially excluded from reactor 13. It will be understood that any propane formed represents a loss of yield of the desired reaction product.

The reaction conditions which are employed in reactors 1 and 13 are generally known. A noble metal promoted titanium silicalite catalyst is suitable for both reaction steps. It is preferred that a single catalyst such as Pd on TS-1 be used in both reactor 1 and 13, but it is feasible that a catalyst mixture, for example Pd on TS-1 together with TS-1 not containing noble metal be used in each reactor. Other mixed catalyst, e.g. Pd on activated carbon in admixture with TS1 can be used.

Preferred titanium containing zeolite catalysts suitable for use in the process of this invention will generally have a composition corresponding to the following empirical formula $xTiO_2$ $(1-x)SiO_2$ where x is between 0.0001 and 0.500. More preferably, the value of x is form 0.01 to 0.125. The molar ratio of Si:Ti in the lattice frame work of the zeolite is advantageously from 9.5:1 to 99.1 (most preferably from 9.5:1 to 60:1). The use of relatively titanium-rich zeolites may also be desirable. The zeolite may or may not contain extra framework titanium.

The catalyst preferably comprises a noble metal supported on the above described zeolites. While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 5 weight percent, preferably 0.05 to 2 weight percent.

The titanium silcalite used is prepared by known procedures. A preferred feature is that the silicalite be subjected to an oxidative calcination as with air at elevated temperature, e.g. 300 to 850° C., illustratively 550° C., in accordance with known procedures prior to use in accordance with the invention. The calcination is carried out until substantially complete removal of organic residues is accomplished. Thorough pre-washing and oxidative calcination procedures are described, for example in JP H-269029 and JP H-269030.

The titanium silicalite washing and calcination is carried out so as to remove essentially all of the residues of materials such as templating agents and the like used in the silicalilte preparation, especially ammonium-type materials.

The calcined silicalite essentially free of residues is then treated as by ion exchange or impregnation procedures in order to incorporate the desired noble metal into the silicalite in appropriate amounts. Of the procedures, ion exchange is preferred with subsequent essentially complete removal of anionic residues from the resulting catalyst. Impregnation procedures can be used as his described herein later.

Removal of essentially all residues from the noble metal containing support is important and is conventionally accomplished by water washing and filtering techniques. Multiple washing and filtering steps are especially preferred. Preferably the noble metal/titanium silicalite catalyst is then dried by gentle heating, for example, under vacuum.

Preferably, the catalyst is subjected to an oxidative calcination at temperatures of at least 150° for illustratively 10 minutes to 24 hours. Calcination temperature in the range 150–650° C., preferably 250–600° C., and most preferably 300–550° C. are employed. Preferably the calcined catalyst is reduced with hydrogen at a lower temperature, e.g. below 100° C., before use.

Additional improvements are also achieved where prior to or during epoxidation in reactor 13 the catalyst is contacted with solutions buffered to slightly acid to basic pH. The preferred pH range is 5–8, preferably 6–7.5. See, for example, U.S. Pat. No. 5,646,314. Especially advantageous is the use of sodium, ammonium, and/or potassium salt buffered solutions. Excellent results are also achieved with calcium and magnesium salt containing solutions. Other Group I a and II a salts can be used as can compounds such as triphenyl phosphine. The combination of the calcination and contact with the buffered solution gives best results.

Preferred is the use of various promoters, such as phosphorous compounds as described in U.S. Pat. No. 6,005,123.

The process of propylene epoxidation may be suitably conducted under the reaction conditions (e.g., temperature, pressure, reactant ratios) described in the following published patent applications: WO 96/102323, WO 97/25143, DE 19600709, WO 97/31711, WO 97/47386, JP 4-352771, JP H8-269029, and H8-269030.

The process of the invention may be suitably conducted in each reaction step under the reaction conditions (e.g., temperature and pressure) described in the following published patent applications. WO 96/02323, WO 97/25143, DE 19600709, WO 97/31711, WO 97/47386, JP 4-352771, JP H8-269029, and H8-269030.

Both reactions are carried out in the liquid phase; it is advantageous to work at a pressure of 1–100 bars and in the presence of one or more solvents. Suitable solvents include, but are not limited to, lower aliphatic alcohols such as methanol, ethanol, isopropanol, and tert-butanol, or mixtures thereof, carbon dioxide, and water. Fluorinated alcohols can be used. It is also possible to use mixtures of the cited alcohols with water.

It is especially useful to use small amounts of HBr e.g. 5–20 ppm, as promoter in the feed to reactor 1.

The reactions according to the invention are each carried out at a temperature effective to achieve the desired reaction, preferably at temperatures in the range of 0–125° C. (more preferably, 20–80° C.). The molar ratio of hydrogen to oxygen can usually be varied in the range of $H_2:O_2-1:10$ to 5:1 and is especially favorable at 1:5 to 2:1. The molar ratio of hydrogen peroxide to olefin is usually 1:1 to 1:20.

Promoters as described in U.S. Pat. Nos. 6,005,123 and 6,008,388 can be used in reactor 13 as above described, especially ammonium phosphate.

The following Examples illustrate the invention.

Example 1

Catalyst Preparation

About 112 parts by weight of spray dried particles of TS-1 (about 30 micron average diameter weighted by volume) comprised of 20 wt % silica binder are slurried in 251 parts by weight deionized water. About 1.3 parts by weight tetra ammine palladium dichloride is dissolved in 90 parts by weight of deionized water. The palladium solution is added to the TS-1 slurry over a 30 minute period with agitation and the mixture is turned at 30 rpm in a 30° C. water bath for 2 hours. The solids are filtered and washed by reslurrying in 140 parts by weight of deionized water and filtering. The solids are washed three more times with 140 parts by weight of deionized water and dried in a vacuum oven at 50° C. for 8 hours to give 109 parts by weight product. The elemental analysis shows; palladium=0.31 wt %, Ti=1.63 wt %. The solids are calcined in air by heating from 23 to 110° C. at 10° C./min and holding at 110° C. for 4 hours, and then heating at 2° C./min to 150° C. and holding for 4 hours.

This Pd/TS-1 is placed in a quartz tube and treated with 5% hydrogen/nitrogen while heating at 50° C. for 4 hours to form active catalyst.

Example 2

Propylene Oxide Production

A 100 mL Parr reactor equipped with a stir bar is charged with 150 mg of Pd/TS-1 (0.3 wt % Pd, prepared as in Example 1), 0.22 mg of an HBr solution prepared by mixing a 48 wt % aqueous solution of hydrogen bromide (0.115 grams) with 100 ml deionized water, one gram of deionized water, one gram of an ammonium phosphate buffer (pH=6, 0.1 M) and 16 grams of methanol. The buffer is prepared by dissolving 11.5 parts by weight ammonium dihydrogen phosphate in 800 parts by weight deionized water, aqueous ammonium hydroxide is added until a pH of 6.0 is obtained; deionized water is added to give 1000 parts by weight solution.

The reactor is pressurized to 500 psig with nitrogen and vented to one atmosphere. The reaction mixture is then heated to 30° C., pressurized to 100 psig of hydrogen followed by 4 vol % oxygen/nitrogen to a total pressure of 1287 psig. The reaction mixture with stirring is allowed to react at 30° C. for 60 minutes, cooled to 10° C., and depressurized to atmospheric pressure; the liquid phase contains 0.38 wt % hydrogen peroxide.

Propylene (7.6 grams) is then charged and the reactor pressurized to 300 psig with nitrogen. The reaction mixture with stirring is heated to 50° C. for 120 minutes, cooled to 10° C., vented to one atmosphere and the liquid phase analyzed by GC. The GC analysis of the liquid phase shows 0.34 wt % propylene oxide as the only propylene derived product.

Example 3

Propylene Oxide Production

A 100 mL Parr reactor equipped with a stir bar is charged with 150 mg of Pd/TS-1 (0.3 wt % Pd, prepared as in Example 1), 0.22 gram of an HBr solution (prepared as in Example 2), one gram of deionized water, one gram of an ammonium phosphate buffer (pH 6, 0.1 M) as described in Example 2, and 16 grams of methanol. The reactor is pressurized to 500 psig with nitrogen and vented to one atmosphere. The reaction mixture is then heated to 30° C., pressurized to 100 psig of hydrogen followed by 4% oxygen/nitrogen to a total pressure of 1287 psig. The reaction mixture with stirring is allowed to react at 30° C. for 60 minutes, cooled to 10° C., and depressurized to atmospheric pressure. The liquid phase contains 0.33 wt % hydrogen peroxide.

Propylene (7.6 grams) is then charged and the reactor pressurized to 300 psig with nitrogen. The reaction mixture with stirring is heated to 30° C. for 60 minutes, cooled to 10° C., vented to one atmosphere and the liquid phase analyzed by GC. The GC analysis of the liquid phase shows 0.38 wt % propylene oxide as the only propylene derived product.

Example 4

Propylene Oxide Production

A 100 mL Parr reactor equipped with a stir bar is charged with 150 mg of Pd/TS-1 (0.3 wt % Pd, prepared as in Example 1), 0.22 gram of an HBr solution (prepared as in Example 2), one gram of deionized water, one gram of an ammonium phosphate buffer (pH=6, 0.1 M) as described in Example 2, and 16 grams of methanol. The reactor is pressurized to 500 psig with nitrogen and vented to one atmosphere. The reaction mixture is then heated to 60° C., pressurized to 100 psig of hydrogen followed by 4% oxygen/nitrogen to a total pressure of 1287 psig. The reaction mixture with stirring is allowed to react at 60° C. for 15 minutes, cooled to 10° C., and depressurized to atmospheric pressure. The liquid phase contains 0.24 wt % hydrogen peroxide.

Propylene is then charged to the reactor and reacted therein as described in Example 3 to form propylene oxide.

Example 5

Continuous Production

The reaction system shown in FIG. 1 is employed for the continuous production of propylene oxide.

Continuously fed to reactor 1 are oxygen and hydrogen in a ratio of 0.7 mols $O_2$ per mol $H_2$. A slurry of 10 wt % Pd on TS-1 catalyst in methanol is also fed at a high rate. The catalyst is prepared as indicated in Example 1.

Included in the feed to reactor 1 is a small amount of acidic phosphates which are formed as later indicated and which enhances hydrogen peroxide production. Also a small amount of e.g. 10 ppm, of HBr promoter is included in the feed.

Reaction conditions in reactor 1 are 50° C., 55 psig, residence time of the liquid is about 10 minutes.

Slurry reaction mixture containing about 0.8 wt % hydrogen peroxide passes to reactor 13 wherein propylene oxide is produced. Also introduced to reactor 13 is propylene in amount of about 1.1 mols propylene per mol of hydrogen peroxide in the stream fed to reactor 13. Hydrogen and oxygen are excluded to the extent feasible in the feed to reactor 13.

In an especially preferred practice, a small amount of a buffer such as ammonium phosphate is useful in the reactor 13 reaction mixture to provide a pH of 6–7 in order to suppress undesirable acid catalyzed ring opening reactions. Generally amounts of buffer effective to keep the reaction mixture in reactor 13 slightly acidic e.g. pH 6–7, are employed. In order to provide this buffering action a small amount of ammonia is added to the reaction mixture passing from reactor 1 to reactor 13 sufficient to react with the phosphoric acid therein and form ammonium phosphate. Ammonium phosphate itself can be added to make up for losses.

Reaction conditions in reactor 13 are 50° C., 45 psig, residence time is about 10 minutes.

Product propyleneoxide is recovered from both the vapor overhead and the recycle reaction mixture slurry from reactor 13; overall propyleneoxide yield based on propylene reacted is about 92%.

In a special feature, the catalyst—containing slurry recycled to reactor 1 from reactor 13 is sent to an inert gas stripper, e.g. a methane stripper, where propylene contained therein is stripped overhead form the slurry and also some of the ammonia derived from the ammonium phosphate buffer is separated by stripping to lower the pH to about a 6–7 level in the slurry recycle to reactor 1.

We claim:

1. The process for preparing propylene oxide which comprises
    a) in a first reaction step reacting hydrogen and oxygen in a solvent/solid catalyst slurry to form hydrogen peroxide, propylene being essentially excluded from the reaction,
    b) introducing propylene into the hydrogen peroxide and catalyst containing reaction mixture from the first reaction step, and c) reacting said hydrogen peroxide in a second reaction step with propylene to form propylene oxide.

2. The process for preparing propylene oxide which comprises a) in a first reaction zone reacting hydrogen and oxygen in a solvent/solid catalyst slurry to form hydrogen peroxide, propylene being essentially excluded from said zone, b) transferring the hydrogen peroxide and catalyst containing reaction mixture to a second reaction zone, and c) reacting said hydrogen peroxide in said second reaction zone with propylene to form propylene oxide.

3. The process of claim 1 wherein the solid catalyst is a noble metal on TS-1 catalyst.

4. The process of claim 3 wherein the noble metal comprises a mixture of noble metals.

5. The process of claim 1 wherein the solid catalyst is a palladium on TS-1 catalyst.

6. The process of claim 1 wherein the solvent is selected from the group consisting of water, $C_1$–$C_4$ alkanols, carbon dioxide, and mixtures thereof.

7. The process of claim 6 wherein the $C_1$–$C_4$ alkanol is methanol.

8. The process of claim 2 wherein the solvent is selected from the group consisting of water, $C_1$–$C_4$ alkanols, carbon dioxide, and mixtures thereof.

9. The process of claim 8 wherein the $C_1$–$C_4$ alkanol is methanol.

* * * * *